United States Patent [19]

Greatbatch

[11] 4,405,311

[45] Sep. 20, 1983

[54] METHOD AND APPARATUS FOR DIRECT ELECTRICAL INJECTION OF GOLD IONS INTO TISSUE SUCH AS BONE

[75] Inventor: Wilson Greatbatch, Clarence, N.Y.

[73] Assignee: Greatbatch Enterprises, Inc., Clarence, N.Y.

[21] Appl. No.: 214,118

[22] Filed: Dec. 8, 1980

[51] Int. Cl.³ ............................................ A61N 1/30
[52] U.S. Cl. ................................. 604/20; 128/419 R
[58] Field of Search ............ 128/68.1, 207.21, 419 R, 128/419 F, 784, 785, 787, 789, 803, 207.22; 604/20, 21

[56] References Cited

U.S. PATENT DOCUMENTS

| 1,967,927 | 7/1934 | Deutsch | 128/207.21 |
| 2,263,205 | 11/1941 | Conrad | 128/207.21 |
| 3,842,841 | 10/1974 | Brighton et al. | 128/419 F |
| 4,027,393 | 6/1977 | Ellis et al. | 128/207.21 |
| 4,292,968 | 10/1981 | Ellis | 128/207.21 |

FOREIGN PATENT DOCUMENTS

| 480202 | 3/1975 | Australia | 128/419 F |
| 2552523 | 8/1976 | Fed. Rep. of Germany | 128/419 F |

OTHER PUBLICATIONS

Jessop, "Gold in the Treatment of Rheumatoid Arthritis", J. of Rheumatology Supp. No. 5, 1978, pp. 12–17.
Dutton, "Ionic Medications", Clinical Med. & Surg, Aug. 1935, vol. 42, No. 8, pp. 386–389.

Primary Examiner—Lee S. Cohen
Attorney, Agent, or Firm—Christel, Bean & Linihan

[57] ABSTRACT

A method and apparatus for treating rheumatoid arthritis by direct injection of electrically generated gold ions into the patient's joint. The gold ions are electrically generated by anodal corrosion of a gold electrode, such as by passing a constant electric current through the gold electrode which can be a thin wire and which is surgically placed in contact with the arthritic joint. The apparatus comprises a source of direct current including a battery and a constant current generator, a gold electrode connected to the source electrically as an anode and adapted to be placed surgically in operative contact with the arthritic joint, and an indifferent electrode connected to the source electrically as a cathode and adapted to be placed in operative contact with the patient's body spaced from the joint. The entire apparatus can be implanted in the patient's body.

12 Claims, 2 Drawing Figures

METHOD AND APPARATUS FOR DIRECT ELECTRICAL INJECTION OF GOLD IONS INTO TISSUE SUCH AS BONE

BACKGROUND OF THE INVENTION

This invention relates to healing of tissue such as bone, and more particularly to a new and improved method and apparatus for providing healing treatment of rheumatoid arthritis.

One area of use of the present invention is providing healing treatment of rheumatoid arthritis at the bone joint, although the principles of the present invention can be variously applied. A conventional treatment for rheumatoid arthritis is the taking of gold salts by mouth over a period of months. By such treatment an attempt is made to build up the systemic level of gold in the body up to about one gram. The results sometimes are spectacular, but the treatment sometimes also is ineffective and severe side effects are often seen. Accordingly, the treatment usually is reserved for a last resort effort and is used when other less traumatic treatments fail.

It would, therefore, be highly desirable to provide a method and apparatus for treating rheumatoid arthritis which can concentrate the gold at the arthritic joint and avoid raising the systemic level of gold to prevent side effects.

SUMMARY OF THE INVENTION

It is, therefore, a primary object of the present invention to provide a new and improved method and apparatus for treating rheumatoid arthritis.

It is a further object of this invention to provide such method and apparatus wherein gold is administered for treatment directly to the arthritic joint.

It is a further object of this invention to provide such method and apparatus wherein gold is administered to the arthritic joint in a manner vastly decreasing the patient's systemic level of gold during the treatment.

It is a further object of this invention to provide such method and apparatus which achieves relatively much higher levels of gold in the arthritic joint without raising the patient's systemic level of gold to traumatic levels.

It is a further object of this invention to provide such apparatus which is implantable in the body of a patient.

The present invention provides a method and apparatus for treating rheumatoid arthritis by direct injection of electrically generated gold ions into the patient's joint. The gold ions are electrically generated by anodal corrosion of a gold electrode, such as by passing a constant electric current through the gold electrode, and the gold electrode, which can be in the form of a thin wire, is surgically placed in contact with the arthritic joint. The apparatus preferably is of the type which is implanted in the body of a patient. In particular, the apparatus comprises a source of constant direct electric current which can include a battery and an electronic constant current generator, a gold electrode connected to the source electrically as an anode and adapted to be placed surgically in operative contact with the arthritic joint, and an indifferent electrode connected to the source electrically as a cathode and adapted to be placed in operative contact with the patient's body spaced from the joint.

The foregoing and additional advantages and characterizing features of the present invention will become clearly apparent upon a reading of the ensuing detailed description toether with the included drawing wherein:

BRIEF DESCRIPTION OF THE DRAWING FIGURES

FIG. 1 is a diagrammatic view of the apparatus of the present invention as it would appear during use implanted in the body of a patient; and FIG. 2 is a schematic circuit diagram of the appratus of the present invention.

DETAILED DESCRIPTION OF THE ILLUSTRATED EMBODIMENTS

Figure 1:
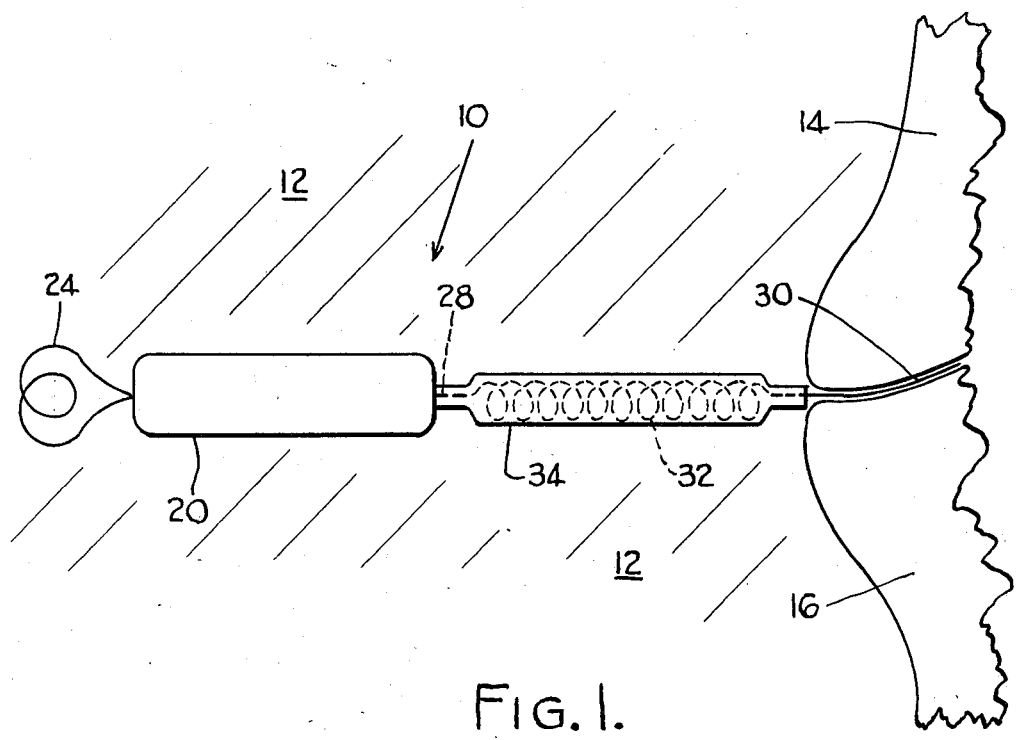

FIG. 1 illustrates the apparatus according to the present invention, generally designated 10, as it would appear implanted in the body of a patient, in particular being situated in body tissue generally designeated 12. The apparatus is illustrated in FIG. 1 for treating rheumatoid arthritis by direct injection of electrically generated gold ions into the patient's joint between two bones represented at 14 and 16. The apparatus includes a housing 20 which contains a d.c. current source including a battery and a constant current generator which will be described in detail presently. The battery and generator are encapsulated in epoxy material which, in turn, is coated with a silicone medical adhesive. As a result, housing 20 is of human body reaction-free material enabling the apparatus to be implanted in the body of the patient near the affected joint. Housing 20 is generally elongated, typically one inch in length and having a width or cross sectional dimensions of about one quarter inch.

The apparatus further comprises a reference or indifferent electrode designated 24 which is connected to the d.c. current source as a cathode in a manner which will be described in detail presently. During use, as illustrated in FIG. 1, the indifferent electrode 24 is in operative contact with the patient's body spaced from the joint being treated. As shown in FIG. 1, electrode 24 is in contact with a region of the tissue 12 spaced from the joint between bones 14,16. In the device shown, indifferent electrode 24 preferably is a wire of silver having a diameter of about 0.02 inch and formed preferably into a doubled loop having an overall dimension of about one quarter inch.

The apparatus further comprises a treating electrode generally designeated 28 of gold which is connected to the d.c. current source to serve as an anode in a manner which will be described in detail presently. During use, treating electrode 28 is adapted to be placed surgically in operative contact with the arthritic joint of the the patient. In the device shown, the treating electrode 28 extends from the end of housing 24 opposite the end from which the indifferent electrode extends. The treating electrode 28 is in the form of a thin wire and includes a monofilament portion 30 at the outer end thereof which is operatively connected to the patient's joint, and a coiled spring portion 32 between the monofilament portion and the end which is connected to the constant current source.

As shown in FIG. 1, when the device is surgically implanted in a patient, the entire monofilament portion 30 is in the patient's joint between the bones 14,16 as shown in FIG. 1. The coiled spring portion 32, which serves to provide stress relief in enabling the wire to withstand the bending stresses encountered in joint motion, is covered by a sheath 34 of silicone rubber which extends along the entire portion thereof. In particular, the silicone sheath 34 abuts housing 24 at one end thereof and the opposite end adjacent the monofilament portion abuts against the patient's joint when the device is implanted. The wire 28 typically has a diameter of 0.010 inch. Since pure gold is relatively soft and may not be able to withstand the bending stresses encountered in joint motion, wire 28 can be formed of a relatively hard orthodontic gold alloy, for example an alloy commercially available from the Williams Gold Refining Company Limited under the designation "orthodontic gold" which contains copper and silver added to the gold along with some additional alloying elements such as palladium, platinium and zinc.

Figure 2:
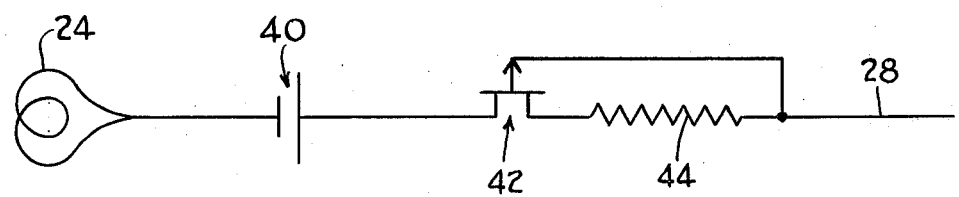

Referring now to FIG. 2, the source of constant direct current within housing 20 comprises a battery 40, the negative terminal of which is connected to indifferent electrode 24. The source further comprises a constant current generator including a field effect transistor 42 and a resistor 44. The positive terminal of battery 40 is connected to the drain terminal of field effect transistor 42, and the source terminal of transistor 42 is connected to one terminal of resistor 44. The other terminal of resistor 44 is connected to treating electrode 28 and to the gate terminal of field effect transistor 42. The controlled current flows through resistor 44 establishing a bias voltage between the source and gate of field effect transistor 42. When the bias voltage reaches a level so as to bias the transistor 42 to pass current sufficient to produce an equal voltage across resistor 44 the circuit becomes a constant source due to the known characteristics of a field effect transistor. By way of example, in an illustrative device, battery 40 is a Mallory WH1T2 having a voltage of 1.35 volts and transistor 42 is a National Semiconductor PN3687 or the equivalent. With the desired current flow being 1.0 microampere and the gate-to-source voltage drop being 0.5 volt, resistor 44 should have a magnitude of about 0.5 megohm.

In operation, the monofilament portion 30 of treating electrode 28 is placed surgically in the affected cartilage in an arthritic joint of the patient. Preferably, the entire device 10 which weighs only a few grams is surgically implanted in tissue 12 adjacent the treatment site as shown in FIG. 1. In response to the flow of electrical current through the gold treating electrode 28, gold ions are generated and injected directly into the patient's joint for treatment. Battery 40 is selected to provide enough energy for several months of gold ion generation. The stimulator current is accurately set and controlled by the constant current generator, in particular by selecting the magnitude of resistor 44 relative to the known voltage of battery 40 and the desired current magnitude as previously described. Typically, the current flowing in treatment electrode 28 during operation of the device is in the range from about 1.0 microampere to about 10.0 microamperes. The number of gold ions released in the arthritic joint is directly calculable from the value of the current flowing in electrode 28 using Faraday's Law. By way of example, with a current of 1.0 microampere $2 \times 10^{12}$ gold ions are released.

The method and apparatus of the present invention thus provides a concentration of all of the generated gold ions in the joint being treated. This advantageously provides much higher levels of gold in the arthritic joint without raising the patient's systemic level of gold to traumatic levels. Actually, the concentration of all the gold in the joint should vastly decrease the patient's systemic level of gold during treatment thereby alleviating any side effects. The foregoing is provided by a device which is relatively simple in construction, reliable in operation and readily implantable in the body of a patient.

It is therefore apparent that the present invention accomplishes its intended objects. While an embodiment of the present invention has been described in detail, this is for the purpose of illustration, not limitation.

I claim:

1. A method for treating rheumatoid arthritis by direct injection of electrically generated gold ions into the joint.

2. A method according to claim 1, wherein said gold ions are electrically generated by anodal corrosion of a gold electrode.

3. A method according to claim 2, wherein said anodal corrosion is performed by passing a constant electric current through said gold electrode.

4. A method according to claim 3, wherein the magnitude of said constant current is in the range from about 1 microampere to about 10 microamperes.

5. A method according to claim 2, wherein said gold electrode is in the form of a wire.

6. A method according to claim 2, wherein said electrode is implanted so as to be operatively connected to said joint.

7. Apparatus for treating rheumatoid arthritis comprising:
    (a) a source of constant direct electric current;
    (b) a treating electrode of gold connected to said source electrically as an anode and adapted to be placed surgically in operative contact with the arthritic joint of a patient, said electrode being in the form of a fine wire having a monofilament portion at the end operatively connected to the joint;
    (c) an indifferent electrode connected to said source electrically as a cathode and adapted to be placed in operative contact with the patient's body spaced from said joint; and
    (d) said current source having a structure which provides a predetermined current magnitude and said monofilament portion of said wire having a diameter which in combination with said predetermined current magnitude produces anodal corrosion of said monofilament portion to release gold ions;
    (e) whereby in response to flow of electrical current through said gold electrode gold ions are generated and injected directly into the joint for treatment.

8. Apparatus according to claim 7, wherein said constant current source comprises a battery and an electronic constant current generator.

9. Apparatus according to claim 7 wherein said gold wire is in the form of a coiled spring between the monofilament portion and the end connected to said constant current source.

10. Apparatus according to claim 7, further including a housing for said apparatus of human body reaction-free material for enclosing said source whereby said apparatus can be implanted in the body of the patient near said joint.

11. Apparatus according to claim 10, wherein said gold electrode has a portion adapted to extend between said housing and said joint and further including a covering enclosing said electrode portion of human body reaction free material.

12. Apparatus according to claim 7, wherein the size of said gold wire is about 0.010 inch in diameter.

* * * * *